United States Patent [19]
Antonelli et al.

[11] Patent Number: 5,767,166
[45] Date of Patent: Jun. 16, 1998

[54] PROCESS FOR PRODUCING MIXTURES OF METHANOL AND HIGHER ALCOHOLS

[75] Inventors: Giambattista Antonelli, Lesmo; Ugo Cornaro, Seriate, both of Italy

[73] Assignee: Snamprogetti S.p.A., Milan, Italy

[21] Appl. No.: 732,597

[22] Filed: Oct. 15, 1996

[30] Foreign Application Priority Data

Oct. 13, 1995 [IT] Italy ................................ MI95A2100

[51] Int. Cl.$^6$ ........................................................ C07C 1/04
[52] U.S. Cl. .......................... 518/714; 518/713; 518/715; 518/717; 502/307; 502/319
[58] Field of Search ........................ 502/307, 319; 518/714, 717, 713, 715

[56] References Cited

U.S. PATENT DOCUMENTS 4,481,012  11/1984  Di Pietro et al. .................. 44/53
4,513,100  4/1985  Fattore et al. ...................... 502/303

FOREIGN PATENT DOCUMENTS 2083469  9/1981  United Kingdom .

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

Process for producing mixtures of methanol and higher alcohols comprising feeding, into the reaction zone equipped with a catalytic system, $H_2$, CO and possibly inert products with a molar ratio $H_2/CO$ of between 0.2 and 10, at a temperature of between 200° and 460° C., at a pressure of between 2,000 and 30,000 KPa, and at a space velocity of between 1,000 and 40,000 GHSV, wherein the catalytic system corresponds to the following empirical formula:

$$Zn_xCr_yO_t + z\% M_2O$$

wherein the x/y ratio is greater than 0.5 and less than 1, t is what is necessary for satisfying the valence with which the various elements appear in the catalyst, M is an alkaline metal selected from potassium and cesium, z, representing the percentage of alkaline oxide of the final catalyst, when the metal is potassium, is between 0.01 and 8 and, when the metal is cesium, between 0.01 and 20.6.

3 Claims, No Drawings

PROCESS FOR PRODUCING MIXTURES OF METHANOL AND HIGHER ALCOHOLS

The present invention relates to a process for producing mixtures of methanol and higher alcohols starting from $H_2$ and CO with the possible presence of $CO_2$ and inert products.

These mixtures produced are particularly useful as substitutes of gasoline and can also be mixed with it in various percentages for use as fuel for internal combustion engines.

Many catalysts are known for the production of methanol mixed with higher alcohols.

"Catalysis-Emmet-(Vol.5) describes a catalyst among others consisting of Cu, ZnO and $Cr_2O_3$ in molar percentages of 82%, 16% and 2% respectively; $K_2O$ must be added to these components to give the necessary selectivity.

Patent CA-273984 describes a catalyst whose composition consists of one or more metallic oxides selected from Ag, Cu, Zn, Mo, U, V, and one or more alkaline or earth-alkaline oxides, wherein the metal oxides must be equal as atoms to at least half of the total number of atoms of the other metals.

In paten FR-2369234 the catalyst consists of Cu, Co, at least one element selected from Cr, Fe, V, Mn, and at least one alkaline metal in rather wide composition ranges.

With all these types of catalyst not very high productivities and selectivities are obtained for the production of methanol and higher alcohols. Moreover these catalysts age rapidly, consequently losing both their activity and selectivity. In addition to these disadvantages mentioned above, it is known that beyond certain temperatures (300° C.) the catalysts containing copper cannot be used owing to methanation.

Most of the drawbacks described above have been overcome by using the catalyst described in U.S. Pat. No. 4,513,100.

The catalyst described therein is represented by the following empirical formula:

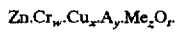

wherein

A is the metal or alkaline metals,

Me is one or more metals selected from molybdenum, manganese, lanthanium, cerium, aluminium, titanium and vanadium, w is between 0.1 and 0.8, preferably between 0.3 and 0.6, x is between 0.005 and 0.05, preferably between 0.01 and 0.03, y is between 0.002 and 0.2, preferably between 0.01 and 0.1, z is between 0 and 0.1, preferably between 0 and 0.04, t is between 3.75 and 1.3 and is what is necessary for satisfying the valence with which the various elements appear in the catalyst.

This catalyst has both a productivity and selectivity which are higher than the catalyst previously used.

The use of this catalyst instead of the previous ones leads to a considerably reduced methanation, whereas the synthesis of methanol takes place with a sufficiently high rate and the hydrogenation of the intermediates gives more stable products.

The identification of catalysts and operating conditions which lead to an increase in the selectivity of isobutanol in the mixture of methanol and higher alcohols is the objective of the latest research projects.

Isobutene is easily obtained from isobutanol by dehydration, from which MTBE is obtained by reaction with methanol, thus obtaining the complete synthesis of MTBE from syngas and therefore from non-petroleum sources.

It is known (P. Forzatti, E. Tronconi, I. Pasquon Catal. Rev. 33,109,1992) that catalysts based on alkalinized Zn/Cr owing to the particular formation mechanism of alcohols produce a mixture wherein isobutanol prevails among the pool of higher alcohols, that an increase in temperature favours the formation of higher alcohols with respect to methanol and that operating at a high GHSV considerable productivities can be obtained.

On the other hand it is known (F. Trifiro', A. Vaccari in Symp. on Structure-Activity Relationships in Heterogeneous Catalysis. ACS Meeting Boston 1990) that the characteristic physico-chemical properties and reactivity of catalysts based on Zn Cr are associated with deviations from the stoichiometric formulation $ZnCr_2O_4$ which allows for example the Zn to be stabilized in unusual co-ordinative environment.

We have verified and will show in the examples below that the action of catalysts previously claimed (IT-22117/A80; IT24659/A80; U.S. Pat. No. 4,513,199) based on Zn Cr modified with alkali under more extreme operating conditions (T=420° C., GHSV=20000 $h^{-1}$ P=180 atm) than those normally used for the synthesis of methanol and higher alcohols enables a productivity to isobutanol of about 200 gr/h/kg to be obtained. These catalysts however do not possess requisites of structural stability which are adequate for maintaining for industrial times of interest the reactivity shown when the operating temperatures are higher than 400° C.

The present invention relates to a process for the preparation of methanol and higher alcohols using a catalytic system which, although maintaining the productivity and selectivity of the catalysts previously claimed, has a greater catalytic stability even when operating under drastic conditions required for obtaining high productivities to isobutanol.

The process, object of the present invention, basically consists in feeding, into the reaction zone equipped with a catalytic system, $H_2$, CO and possibly $CO_2$ and inert products with a molar ratio $H_2/CO$ of between 0.2 and 10, preferably between 0.5 and 2, at a temperature of between 200° and 460° C., preferably between 350° and 440° C., at a pressure of between 2,000 and 30,000 KPa, preferably between 10,000 and 25,000, and at a GHSV space velocity of between 1,000 and 40,000 $h^{-1}$, preferably between 10,000 and 30,000, and is characterized in that the catalytic system corresponds to the following empirical formula:

wherein the ratio x/y is greater than 0.5 and less than 1, preferably between 0.55 and 0.85, even more preferably about 0.75, t is what is necessary for satisfying the valence with which the various elements appear in the catalyst, M is an alkaline metal selected from potassium and cesium, z, representing the percentage of alkaline oxide of the final catalyst, when the metal is potassium, is between 0.01 and 8, preferably between 2 and 5, and, when the metal is cesium, between 0.01 and 20,6, more preferably between 5.8 and 13.6.

The gaseous mixture used for the formation reaction of alcohols can be the synthesis gas obtained for example by the partial combustion of carbon, natural gas or hydrocarbons.

The process is embodied by putting the gaseous mixture in contact with the catalytic system in a suitable reactor which can be either a fluid-bed or fixed-bed reactor.

The preparation of the catalyst can be carried out by means of the following unitary operations:
Coprecipitation
Maturation of the precipitate
Separation of the precipitation
Washings
Thermal treatments
Impregnation with alkali
Thermal treatment The unitary operations necessary for the preparation of the catalyst of the present invention are carried out as described hereunder.

An aqueous solution containing soluble salts, preferably nitrates, Zn and Cr (Soluzione M), is prepared. The molar ratios of Zn and Cr in solution are between 0.5 and 1.

An aqueous solution containing a hydroxide or carbonate or bicarbonate of an alkaline metal or of ammonium or tera alkylammonium (solution P), is prepared.

The precipitation can be carried out by adding solution P to solution M, solution M to solution P or preferably by contemporaneously feeding solution M and solution P into a reaction container.

In the latter case the precipitation can be carried out in such a way as to keep the pH constant by varying the flow rate of the reagents or alternatively by operating with a constant molar ratio Precipitant/Metals and maintaining the flow rate of the two solutions constant.

When the pH is constant, the pH can be selected within the range 5–8. The fluctuations around the preset pH value must be kept within 0.5 units of pH.

When the P/M ratio is constant this value can be selected within the range 1.5–3.5.

The precipitation can be carried out at a temperature selected within the range 25°–80° C.

The maturation of the precipitate is carried out in mother liquor for at least 0.5–4 hours under stirring followed by a decantation period of 0.5–24 hours.

The precipitate is separated by filtration and subjected to washing until the nitrates in the washing water have disappeared.

The solid is dried at 120°–150° C.

Particular attention should be paid to the calcination of the catalyst which is carried out in a stream of reducing gas such as for example hydrogen diluted in nitrogen or preferably in a stream of inert gas such as nitrogen. The catalyst is brought to a temperature of 380°–420° C. with a heating rate of 50°–200° C./hour and maintained at the preset temperature for 0.5–5 hours.

The alkaline metal is introduced by impregnation of the calcined catalyst with aqueous solutions of carbonate, acetate, formiate or other soluble salt of K or Cs.

After impregnation the catalyst is again dried.

Some examples are given below to provide a better illustration of the invention but do not limit the scope of the invention itself.

EXAMPLES

Examples 1–9 describe the preparative procedures of the catalysts within the range Zn/Cr 0.55–0.85.

The catalysts obtained as described in examples 10, 11 and 12 are not an object of the present invention and are included for comparative purposes.

Example 10 provides as a comparison the preparative procedure used for a catalyst with the formulation Zn/Cr=1.

Example 11 provides as a comparison the preparative procedure used for a catalyst with the formulation Zn/Cr=2.

Example 12 provides as a comparison the preparative procedure used for a catalyst with the formulation Zn/Cr=2.6.

Example 1

The reactive precipitant is a solution of $(NH_4)HCO_3$ 2.0M
The solution of metals (800 cc 1.50 total moles of Metals/liter) is prepared by dissolution of the nitrates of Zn and Cr in such a quantity as to obtain a molar composition Zn/Cr= 0.75.

The solution of metals and the solution of $(NH_4)HCO_3$ are contemporaneously added, by means of metering pumps, to 300 cc of solution 0.5M of $(NH_4)HCO_3$ brought to pH 6 and placed in a reaction flask equipped with a stirrer.

The precipitation is carried out at room temperature under conditions of vigorous stirring.

The solution of metals is fed at a flow rate of 8.0 cc/min. The solution of $(NH_4)HCO_3$ is fed with a variable flow rate which is such as to keep the pH within the range of 5.9–6.1.

The precipitation requires 100 minutes. 1600 cc of solution of $(NH_4)HCO_3$ are fed obtaining an average molar ratio $CO_3$/Metals equal to 2.67.

The aging of the precipitate is carried out maintaining the suspension under stirring for 4 hours.

The pH evolves spontaneously reaching a value within the range of 6.8–7.2.

The suspension is left to decant for 12 hours after which the precipitate is separated from the mother liquor.

The precipitate is subjected to a series of washings-filtration until the nitrates have disappeared from the washing water.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 2

The reactive precipitant is a solution of $(NH_4)_2CO_3$ 2.0M
The solution of metals (400 cc 1.50 total moles of Metals/liter) is prepared by dissolution of the nitrates of Zn and Cr in such a quantity as to obtain a molar composition Zn/Cr= 0.75.

The solution of metals and the solution of $(NH_4)_2CO_3$ are contemporaneously added by means of metering pumps to 300 cc of solution 0.1M of $(NH_4)_2CO_3$ brought to pH 6 and placed in a reaction flask equipped with a stirrer.

The precipitation is carried out at room temperature under conditions of vigorous stirring.

The solution of metals is fed at a flow rate of 4.0 cc/min. The solution of $(NH_4)_2CO_3$ is fed with a variable flow rate which is such as to keep the pH within the range of 5.9–6.1.

The precipitation requires 100 minutes. 440 cc of solution of $(NH_4)2CO_3$ are fed obtaining an average molar ratio $CO_3$/Metals equal to 1.47.

The aging of the precipitate is carried out maintaining the suspension under stirring for 4 hours.

The pH evolves spontaneously reaching a value within the range of 6.8–7.2.

The suspension is left to decant for 12 hours after which the precipitate is separated from the mother liquor.

The precipitate is subjected to a series of washings-filtration until the nitrates have disappeared from the washing water.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 3

The same procedure is adopted as described as in example 2 carrying out the precipitation and aging of the precipitate at 65°±5° C.

The decantation takes place in 12 hours under cooling.

The calcined catalyst is finally impregnated with an aqueous solution of K carbonate so that the content of potassium oxide in the final catalyst is 3% by weight. After impregnation the catalyst is again dried.

Example 4

The reactive precipitant is a solution of $(NH_4)_2CO_3$ 2.0M
The solution of metals (400 cc 1.50 total moles of Metals/liter) is prepared by dissolution of the nitrates of Zn and Cr in such a quantity as to obtain a molar composition Zn/Cr=0.75.

The solution of metals and the solution of $(NH_4)_2CO_3$ are contemporaneously added, by means of metering pumps, to 300 cc of solution 0.1M of $(NH_4)_2CO_3$ brought to pH 7 and placed in a reaction flask equipped with a stirrer.

The precipitation is carried out at room temperature under conditions of vigorous stirring.
The solution of metals is fed at a flow rate of 4.0±0.2 cc/min. The solution of $(NH_4)_2CO_3$ is fed with a variable flow rate which is such as to keep the pH within the range of 5.9–6.1.

The precipitation requires 100±5 minutes. 512 cc of solution of $(NH_4)_2CO_3$ are fed obtaining an average molar ratio $CO_3$/Metals equal to 1.7.

The aging of the precipitate is carried out maintaining the suspension under stirring for 4 hours.

The pH evolves spontaneously reaching a value within the range of 6.8–7.2.

The suspension is left to decant for 12 hours after which the precipitate is separated from the mother liquor.

The precipitate is subjected to a series of washings-filtration until the nitrates have disappeared from the washing water.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 5

The reactive precipitant is a solution of $(NH_4)_2CO_3$ 2.0M
The solution of metals (600 cc 1.50 total moles of Metals/l) is prepared by dissolution of the nitrates of Zn and Cr in such a quantity as to obtain a molar composition Zn/Cr=0.75.

The solution of metals and the solution of $(NH_4)_2CO_3$ are contemporaneously added, by means of metering pumps, to 300 cc of water placed in a reaction flask equipped with a stirrer.

The precipitation is carried out at room temperature under conditions of vigorous stirring.
The flow rate of the pumps is regulated so that a constant ratio Precipitant/metals equal to 2 is instantaneously maintained.

600 cc of the solution of metals (10.05 cc/min) and 900 cc of the solution of $(NH_4)_2CO_3$ are fed over a period of 60 minutes.

The aging of the precipitate is carried out maintaining the suspension under stirring for 0.5 hours.

The suspension is subjected to a series of washings-filtration until the nitrates have disappeared from the washing water.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 6

The reactive precipitant is a solution of $(NH_4)_2CO_3$ 2.0M
The solution of metals (600 cc 1.50 total moles of Metals/l) is prepared by dissolution of the nitrates of Zn and Cr in such a quantity as to obtain a molar composition Zn/Cr=0.75.

The solution of metals and the solution of $(NH_4)_2CO_3$ are contemporaneously added, by means of metering pumps, to 300 cc of water placed in a reaction flask equipped with a stirrer.

The precipitation is carried out at room temperature under conditions of vigorous stirring.
The flow rate of the pumps is regulated so that a constant ratio Precipitant/metals equal to 2 is instantaneously maintained.

600 cc of the solution of metals (10.05 cc/min) and 900 cc of the solution of $(NH_4)_2CO_3$ are fed over a period of 60 minutes.

The aging of the precipitate is carried out maintaining the suspension under stirring for 0.5 hours.

The suspension is subjected to a series of washings-filtration until the nitrates have disappeared from the washing water.

The precipitate is finally dispersed in 1000 cc of water and atomized.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 7

The reactive precipitant is a solution of $(NH_4)HCO_3$ 2.0M
The solution of metals (400 cc 1.50 total moles of Metals/liter) is prepared by dissolution of the nitrates of Zn and Cr in such a quantity as to obtain a molar composition Zn/Cr=0.65.

The solution of metals and the solution of $(NH_4)HCO_3$ are contemporaneously added, by means of metering pumps, to 300 cc of solution 0.5M of $(NH_4)HCO_3$ brought to pH 6 and placed in a reaction flask equipped with a stirrer.

The precipitation is carried out at room temperature under conditions of vigorous stirring.
The solution of metals is fed at a flow rate of 4 cc/min.
The solution of $(NH_4)HCO_3$ is fed with a variable flow rate which is such as to keep the pH within the range of 5.9–6.1.

The precipitation requires 100 minutes. 826 cc of solution of $(NH_4)HCO_3$ are fed obtaining an average molar ratio $CO_3$/Metals equal to 2.8.

The aging of the precipitate is carried out maintaining the suspension under stirring for 4 hours.

The pH evolves spontaneously reaching a value within the range of 6.8–7.2.

The suspension is left to decant for 12 hours after which the precipitate is separated from the mother liquor.

The precipitate is subjected to a series of washings-filtration until the nitrates have disappeared from the washing water.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 8

The reactive precipitant is a solution of $(NH_4)HCO_3$ 2.0M
The solution of metals (400 cc 1.50 total moles of Metals/liter) is prepared by dissolution of the nitrates of Zn and Cr in such a quantity as to obtain a molar composition Zn/Cr= 0.55.

The solution of metals and the solution of $(NH_4)HCO_3$ are contemporaneously added, by means of metering pumps, to 300 cc of solution 0.5M of $(NH_4)HCO_3$ brought to pH 6 and placed in a reaction flask equipped with a stirrer.

The precipitation is carried out at room temperature under conditions of vigorous stirring.

The solution of metals is fed at a flow rate of 4 cc/min.
The solution of $(NH_4)HCO_3$ is fed with a variable flow rate which is such as to keep the pH within the range of 5.9–6.1.

The precipitation requires 100 minutes. 838 cc of solution of $(NH_4)HCO_3$ are fed obtaining an average molar ratio $CO_3$/Metals equal to 2.8.

The aging of the precipitate is carried out maintaining the suspension under stirring for 4 hours.

The pH evolves spontaneously reaching a value within the range of 6.8–7.2.

The suspension is left to decant for 12 hours after which the precipitate is separated from the mother liquor.

The precipitate is subjected to a series of washings-filtration until the nitrates have disappeared from the washing water.

The drying is carried out in an oven at 110° C. for 12 hours.

The calcined catalyst is finally impregnated with an aqueous solution of K carbonate so that the content of potassium oxide in the final catalyst is 3% by weight. After impregnation the catalyst is again dried.

The calcination is carried out in a nitrogen stream at 400° C. for 4 hours.

Example 9

The reactive precipitant is a solution of $(NH_4)HCO_3$ 2.0M
The solution of metals (800 cc 1.50 total moles of Metals/liter) is prepared by dissolution of the nitrates of Zn and Cr in such a quantity as to obtain a molar composition Zn/Cr= 0.85.

The solution of metals and the solution of $(NH_4)HCO_3$ are contemporaneously added, by means of metering pumps, to 300 cc of solution 0.5M of $(NH_4)HCO_3$ brought to pH 6 and placed in a reaction flask equipped with a stirrer.

The precipitation is carried out at room temperature under conditions of vigorous stirring.

The solution of metals is fed at a flow rate of 8.0 cc/min.
The solution of $(NH_4)HCO_3$ is fed with a variable flow rate which is such as to keep the pH within the range of 5.9–6.1.

The precipitation requires 100 minutes. 1600 cc of solution of $(NH_4)HCO_3$ are fed obtaining an average molar ratio $CO_3$/Metals equal to 2.67.

The aging of the precipitate is carried out maintaining the suspension under stirring for 4 hours.

The pH evolves spontaneously reaching a value within the range of 6.8–7.2.

The suspension is left to decant for 12 hours after which the precipitate is separated from the mother liquor.

The precipitate is subjected to a series of washings-filtration until the nitrates have disappeared from the washing water.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 10

Comparative

The reactive precipitant is a solution of $(NH_4)_2CO_3$ 2.0M
The solution of metals (600 cc 1.50 total moles of Metals/l) is prepared by dissolution of the nitrates of Zn and Cr in such a quantity as to obtain a molar composition Zn/Cr=1.

The solution of metals and the solution of $(NH_4)_2CO_3$ are contemporaneously added, by means of metering pumps, to 300 cc of water placed in a reaction flask equipped with a stirrer.

The precipitation is carried out at room temperature under conditions of vigorous stirring.

The flow rate of the pumps is regulated so that a constant ratio Precipitant/metals equal to 1.84 is instantaneously maintained.

600 cc of the solution of metals (10 cc/min) and 830 cc of the solution of $(NH_4)_2CO_3$ are fed over a period of 60 minutes.

The aging of the precipitate is carried out maintaining the suspension under stirring for 0.5 hours.

The suspension is subjected to a series of washings-filtration until the nitrates have disappeared from the washing water.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 11

Comparative

The reactive precipitant is a solution of $(NH_4)_2CO_3$ 2.0M
The solution of metals (200 cc 1.50 total moles of Metals/l) is prepared by dissolution of the nitrates of Zn and Cr in such a quantity as to obtain a molar composition Zn/Cr=2.

The solution of metals and the solution of $(NH_4)_2CO_3$ are contemporaneously added, by means of metering pumps, to 300 cc of water placed in a reaction flask equipped with a stirrer.

The precipitation is carried out at room temperature under conditions of vigorous stirring.

The flow rate of the pumps is regulated so that a constant ratio Precipitant/metals equal to 1.8 is instantaneously maintained.

200 cc of the solution of metals (3.33 cc/min) and 270 cc of the solution of $(NH_4)_2CO_3$ are fed over a period of 60 minutes.

The aging of the precipitate is carried out maintaining the suspension under stirring for 0.5 hours.

The suspension is subjected to a series of washings-filtration until the nitrates have disappeared from the washing water.

The drying is carried out in an oven at 110° C. for 12 hours.

The calcination is carried out in a nitrogen stream at 400° C. for 4 hours.

The calcined catalyst is finally impregnated with an aqueous solution of K carbonate so that the content of potassium oxide in the final catalyst is 3% by weight. After impregnation the catalyst is again dried.

Example 12

A catalyst is prepared with a molar ratio Zn/Cr equal to 2.6 operating as described in example 1 of the patent U.S. Pat. No. 4,513,100.

Example 13

Some of the catalysts prepared as described in the examples are subjected to a catalytic test carried out as follows:

4.56 gr of catalyst (7.6 cc) granulated to 14–20 mesh and diluted with 9 cc of quartz are placed in a tubular reactor equipped with a sheath with a co-axial thermocouple. The resulting height of the catalytic bed is about 100 mm. When there is no reaction the isotherm zone of the reactor is about 120 mm. The reactor is placed in a fluidized sand bath.

The catalyst is activated.

The temperature is brought to 200° C., in a stream of $CO/H_2$ at 20 Bar and 20000 $^{-1}$ of GHSV, with a temperature increase-rate of 100° C./h it rises to 300° C. with a temperature increase-rate of 50° C./h 420° C. are finally reached with a temperature increase-rate of 20° C./h. This temperature is maintained for 4 hours, the temperature is lowered to 380° C., the plant is pressurized to 180 bar and the operating temperature is gradually brought back to 420° C.

The reaction is carried out by feeding Syn-gas without $CO_2$ ($H_2/CO=1$). The operating conditions are 180 bar of pressure, a GHSV of 20000 Nl/h/Kg cat and a temperature of 420° C.

Table 1 shows the trend of the productivity time to isobutanol expressed as gr/h/Kg catalyst.

The results obtained clearly show that catalysts with a ratio Zn/Cr within the range of 2.6–1 although providing initial productivities to isobutanol of more than 200 gr/h/Kg are not capable of maintaining this productivity for times of industrial interest.

Viceversa, the catalysts of the present invention maintain high productivities for times of industrial interest.

Example 14

The structural stability is a necessary requisite for maintaining the reactivity for industrial times.

A structural examination was carried out on fresh catalysts and on catalysts discharged after catalytic reaction carried out as described in example 13.

X-ray diffraction techniques were used. In particular the quantitative evaluation of ZnO was carried out by means of full profile fitting techniques.

The results are shown in the following table.

The results obtained clearly show that the more the molar ratio Zn/Cr of the initial formulate exceeds the value of 0.75, the greater the tendency to segregate ZnO will be.

With the evolution of ZnO the ratio Zn/Cr in the residual phase is lowered.

The ratio Zn/Cr evolves over a period of time until a limit value is reached estimated within the range of 0.70–0.75.

A catalyst prepared with an initial ratio Zn/Cr within the range of 0.75 consequently has the characteristics necessary for maintaining its structural stability for times of industrial interest.

TABLE I

| | | Isobutanol productivity (gr/h/Kgcat)/running hours | | | | |
|---|---|---|---|---|---|---|
| Ex. | Zn/Cr | <200h | 200–400h | 400–600h | 600–1200h | >1200h |
| 12 | 2.6 | 210/100h | 190/300h | 180/500h | 140/1000h | |
| 10 | 1 | 225/100h | 195/300h | 195/500h | 180/1130h | 150/1800h |
| 9 | 0.85 | 210/100h | 205/300h | 200/500h | 195/1130h | 190/1100h |
| 6 | 0.75 | 214/100h | 200/300h | 197/500h | 206/1060h | 199/1200h |
| 4 | 0.75 | 225/92h | 235/260h | | | |
| 2 | 0.75 | 230/120h | 230/310h | | | |
| 1 | 0.75 | 275/100h | 275/300h | | | |

TABLE II

| | | | Structural parameters | | | | |
|---|---|---|---|---|---|---|---|
| | Fresh | | Short time discharge | | | Long time discharge | |
| Ex. | %Zn O | Zn/Cr (bulk) | hrs | %Zn O | Zn/Cr (residual phase) | hrs | %Zn O | Zn/Cr (residual phase) |
| 12 | 5 | 2.6 | 305 | 34.7 | 1.38 | 1010 | 40.4 | 1.17 |
| 11 | 0 | 2 | 500 | 34.5 | 1 | | | |
| 10 | 0 | 1 | 345 | 11.3 | 0.78 | 2080 | 14.6 | 0.72 |

TABLE II-continued

| | | | Structural parameters | | | | | |
| | | Fresh | | Short time discharge | | | Long time discharge | |
| Ex. | %Zn O | Zn/Cr (bulk) | hrs | %Zn O (residual phase) | Zn/Cr | hrs | %Zn O (residual phase) | Zn/Cr |
|---|---|---|---|---|---|---|---|---|
| 9 | 0 | 0.85 | 500 | 1.4 | 0.75 | 1100 | 2 | 0.75 |
| 2 | 0 | 0.75 | 520 | 0 | 0.75 | | | |

We claim:

1. Process for the production of mixtures of methanol and higher alcohols comprising feeding, into the reaction zone equipped with a catalytic system, $H_2$, CO and optionally inert products with a molar ratio $H_2/CO$ of between 0.2 and 10, at a temperature of between 200° and 460° C., at a pressure of between 2,000 and 30,000 KPa, and at a space velocity of between 1,000 and 40,000 GHSV, characterized in that the catalytic system corresponds to the following empirical formula:

$$Zn_xCr_yO_t + z\%M_2O$$

wherein the x/y ratio is greater than 0.5 and less than 1, t is what is necessary for satisfying the valence with which the various elements appear in the catalyst, M is an alkaline metal selected from potassium and cesium, z, representing the percentage of alkaline oxide of the final catalyst, when the metal is potassium, is between 0.01 and 8 and, when the metal is cesium, between 0.01 and 20.6.

2. Process according to claim 1 wherein in the catalytic system the ratio x/y is between 0.55 and 0.85, z, when the metal is potassium, is between 2 and 5, and, when the metal is cesium, between 5.8 and 13.6.

3. Process according to claim 1 wherein the molar ratio $H_2/CO$ is between 0.5 and 2, the temperature is between 350° and 440° C., the pressure is between 10,000 and 25,000 KPa, and the GHSV space velocity is between 10,000 and 30,000 $h^{-1}$.

* * * * *